US012324694B2

(12) United States Patent
Lee et al.

(10) Patent No.: US 12,324,694 B2
(45) Date of Patent: Jun. 10, 2025

(54) X-RAY SENSING MODULE

(71) Applicant: InnoCare Optoelectronics Corporation, Tainan (TW)

(72) Inventors: Yi-Chen Lee, Tainan (TW); Chin-Chi Chen, Tainan (TW)

(73) Assignee: InnoCare Optoelectronics Corporation, Tainan (TW)

( * ) Notice: Subject to any disclaimer, the term of this patent is extended or adjusted under 35 U.S.C. 154(b) by 294 days.

(21) Appl. No.: 18/188,439

(22) Filed: Mar. 22, 2023

(65) Prior Publication Data
US 2023/0337996 A1 Oct. 26, 2023

(30) Foreign Application Priority Data
Apr. 25, 2022 (TW) .................. 111115585

(51) Int. Cl.
*A61B 6/00* (2024.01)
*A61B 6/42* (2024.01)

(52) U.S. Cl.
CPC . *A61B 6/42* (2013.01); *A61B 6/54* (2013.01)

(58) Field of Classification Search
CPC ......... G06T 2207/10116; H10F 39/802; H10F 39/12; H10F 39/014; H10F 39/016; H10F 39/803; H10F 39/10; H10F 39/80; H10F 39/807; H10F 77/00; H10F 77/10; A61B 2562/02; A61B 2562/00; A61B 2562/04; A61B 2562/06; A61B 2562/043; A61B 2562/046; A61B 2562/063; A61B 2562/066
See application file for complete search history.

(56) References Cited

U.S. PATENT DOCUMENTS 8,903,048 B2  12/2014  Kitano et al.

FOREIGN PATENT DOCUMENTS

CN  101836867       7/2012
CN  114765192 A  *  7/2022  ....... H01L 27/14603

* cited by examiner

*Primary Examiner* — Don K Wong
(74) *Attorney, Agent, or Firm* — JCIPRNET

(57) ABSTRACT

An X-ray sensing module includes a substrate, multiple normal pixels, and at least two dark pixels. The substrate includes a sensing area. The sensing area has four corners in a top view direction. The normal pixels are disposed in the sensing area and are configured to sense light signals. The at least two dark pixels are respectively disposed at different positions in the sensing area. A distance between the at least two dark pixels and an edge of the sensing area is ¼ to ¹⁄₃₅₀ of a length of the edge.

20 Claims, 8 Drawing Sheets

X-RAY SENSING MODULE

CROSS-REFERENCE TO RELATED APPLICATION

This application claims the priority benefit of Taiwan application serial no. 111115585, filed on Apr. 25, 2022. The entirety of the above-mentioned patent application is hereby incorporated by reference herein and made a part of this specification.

BACKGROUND

Technical Field

The disclosure relates to a sensing module, and in particular to an X-ray sensing module.

Description of Related Art

By using the high penetration characteristics of X-rays, an X-ray sensing module can perform detection without destroying the detection object. Currently, the X-ray sensing module may be applied to medical detection imaging and/or non-destructive industrial detection. For example, the X-ray sensing module may be widely applied to personal biometric checks, airport luggage security checks, or passenger security checks, etc. Therefore, the quality requirements for the X-ray sensing module are also increasing.

SUMMARY

The disclosure provides an X-ray sensing module, which may improve the accuracy or precision of positioning.

The X-ray sensing module of the disclosure includes a substrate, multiple normal pixels, and at least two dark pixels. The substrate includes a sensing area. The sensing area has four corners in a top view direction. The normal pixels are disposed in the sensing area and are configured to sense light signals. The at least two dark pixels are respectively disposed at different positions in the sensing area. A distance between the at least two dark pixels and an edge of the sensing area is ¼ to ⅟₅₀ of a length of the edge.

In order to make the aforementioned features and advantages of the disclosure comprehensible, embodiments accompanied with drawings are described in detail as follows.

DESCRIPTION OF THE EMBODIMENTS

Figure 1:
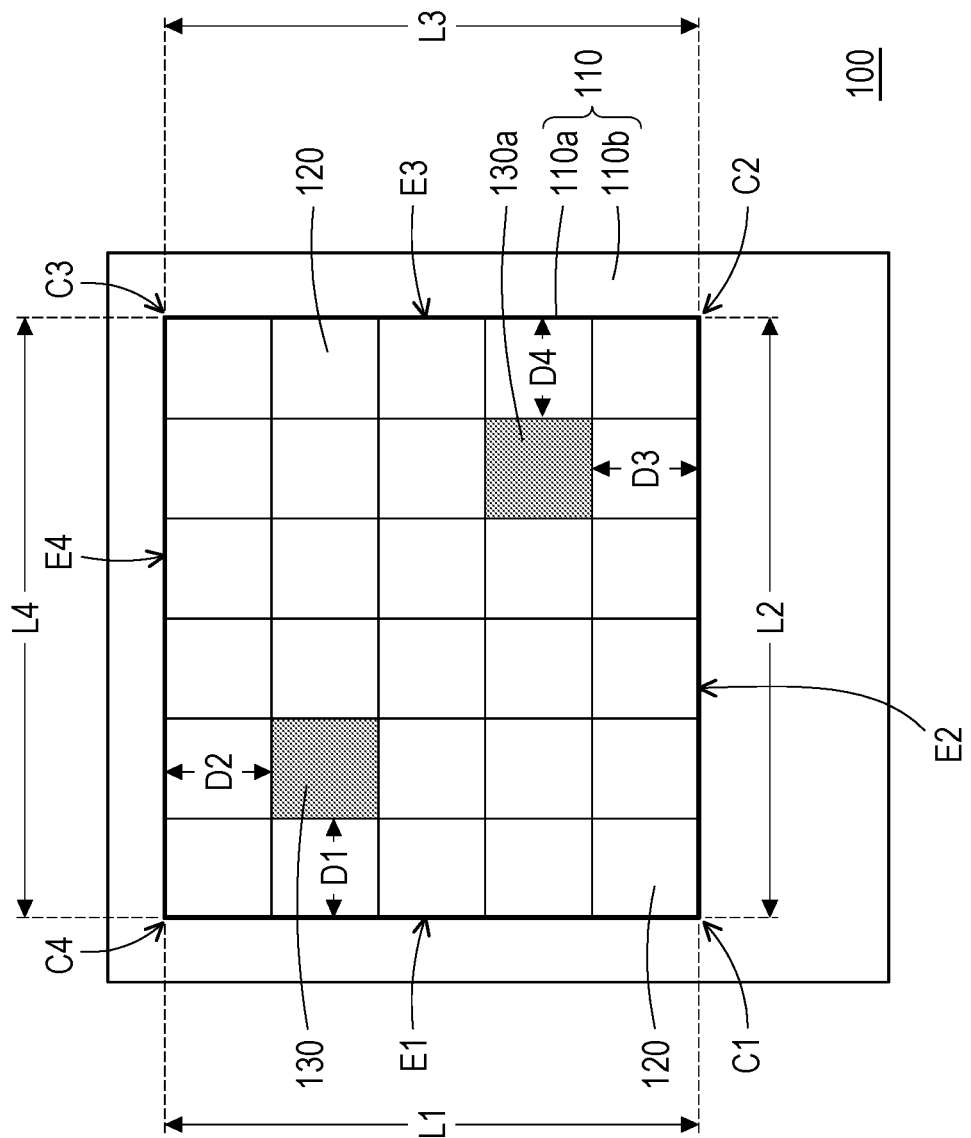
FIG. 1 is a schematic top view of an X-ray sensing module according to a first embodiment of the disclosure.

The disclosure may be understood by referring to the following detailed description combined with the accompanying drawings. It should be noted that, in order to make the readers understand easily and for the simplicity of the drawings, several drawings in the disclosure merely depict a part of the electronic device. Also, certain elements in the drawings are not drawn to actual scale. In addition, the number and size of each element in the figure are merely for illustration, and are not intended to limit the scope of the disclosure.

In the description and claims below, words such as "including" and "comprising" are open-ended words, so they should be interpreted as the meaning of "including but not limited to . . . ."

It should be understood that when an element or a film layer is referred to as being "on" or "connected to" another element or film layer, it may be directly on the another element or film layer or be directly connected to the another element or layer, or there is an intervening element or film layer between the two (indirect cases). In contrast, when an element is referred to as being "directly on" or "directly connected to" another element or film layer, there are no intervening elements or layers between the two.

In the text, the terms "about", "around", "substantially", and "approximately" usually represent within 10%, or within 5%, or within 3%, or within 2%, or within 1%, or within 0.5% of a given value or range. The quantities given here are approximate quantities, that is, the meaning of "about", "around", "substantially", and "approximately" may still be implied in the case where the description of "about", "around", "substantially", and "approximately" are not specified.

In some embodiments of the disclosure, terms such as "connected" and "interconnected" related to joining and connecting, unless otherwise specified, may mean that two structures are in direct contact, or may also mean that two structures are not in direct contact, and there are other structures disposed between these two structures. Moreover, the terms related to joining and connecting may also include the situation that both structures are movable, or both structures are fixed. In addition, the term "coupled" includes any direct and indirect means of electrical connection.

In some embodiments of the disclosure, an optical microscopy (OM), a scanning electron microscope (SEM), a thin film thickness profilometer (α-step), an ellipsometer, or other suitable ways to measure the area, width, thickness or height of each element, or the distance or spacing between elements. In detail, according to some embodiments, a scanning electron microscope may be used to obtain a cross-sectional structure image including the elements to be measured, and measure the area, width, thickness or height of each of the elements, or the distance or spacing between the elements.

The sensing module of the disclosure may be applied to an X-ray sensing module or a fingerprint reader, but is not limited thereto. In addition, the sensing module includes a bendable sensing module or a flexible sensing module. The shape of the sensing module may be rectangular, circular, polygonal, with curved edges or other suitable shapes. The sensing module may have peripheral systems such as a driving system, a control system, a shelf system, etc. to support the X-ray sensing module or the fingerprint reader.

The content of the disclosure is described below with the X-ray sensing module, but the disclosure is not limited thereto.

It should be noted that in the following embodiments, without departing from the spirit of the disclosure, features in several different embodiments may be replaced, reorganized, and mixed to complete other embodiments. As long as the features of the various embodiments do not violate the spirit of the disclosure or conflict with each other, the various embodiments may be mixed and matched arbitrarily.

Reference is now made in detail to the exemplary embodiments of the disclosure, and examples of which are illustrated in the accompanying drawings. If applicable, the same reference numerals in the drawings and the descriptions indicate the same or similar parts.

In the disclosure, an electronic device may include a display module, a sensing module or a splicing module, but is not limited thereto. The electronic device may be a bendable or flexible electronic device. The display module may be a non-self-illuminating display module or a self-illuminating display module. The sensing module may be a sensing module for sensing capacitance, light, heat or ultrasonic, but not limited thereto. Electronic elements may include passive elements and active elements, such as capacitors, resistors, inductors, diodes, transistors, and the like. The splicing module may be, for example, a display splicing module or a sensing splicing module, but not limited thereto. It should be noted that the electronic device may be any permutation and combination of the aforementioned, but not limited thereto. The content of the disclosure is described below with the X-ray sensing module, but the disclosure is not limited thereto.

Figure 2A:
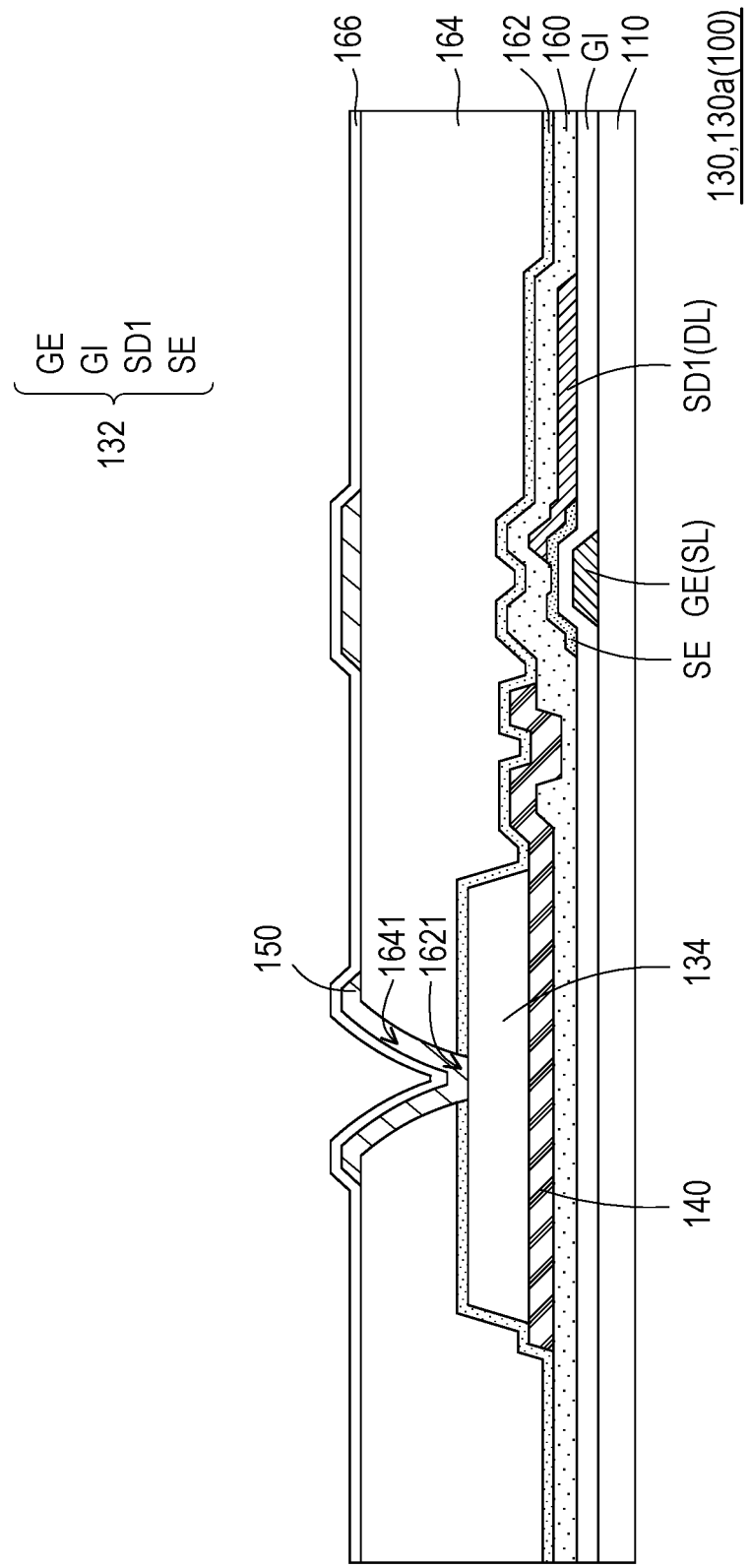
FIG. 2A is a schematic cross-sectional view of dark pixels of the X-ray sensing module in FIG. 1.
Figure 2B:
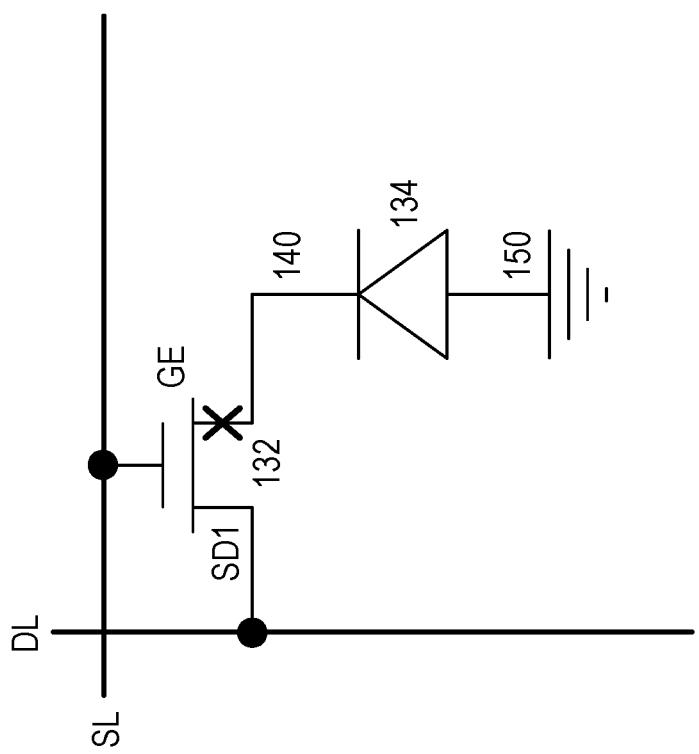
FIG. 2B is a schematic circuit diagram of the dark pixel in FIG. 2A.

FIG. 1 is a schematic top view of an X-ray sensing module according to a first embodiment of the disclosure. FIG. 2A is a schematic cross-sectional view of dark pixels of the X-ray sensing module in FIG. 1. FIG. 2B is a schematic circuit diagram of the dark pixel in FIG. 2A. For clarity and convenience of illustration, some elements in the X-ray sensing module are omitted in FIG. 1.

Referring to FIG. 1, an X-ray sensing module 100 of the embodiment includes a substrate 110, multiple normal pixels 120 (28 are schematically taken as an example in FIG. 1, but not limited thereto) and at least two dark pixels 130 and 130a (two are schematically taken as an example in FIG. 1, but not limited thereto). The substrate 110 may be a rigid substrate, a flexible substrate or a combination thereof. For example, the material of the substrate 110 may include glass, quartz, sapphire, ceramics, polycarbonate (PC), polyimide (PI), polyethylene terephthalate (PET), other suitable materials, or a combination thereof, but not limited thereto.

The substrate 110 includes a sensing area 110a and a non-sensing area 110b. The sensing area 110a is disposed adjacent to the non-sensing area 110b. In some embodiments, the non-sensing area 110b may surround the sensing area 110a, but not limited thereto. In the embodiment, in the schematic top view of the X-ray sensing module 100 (as shown in FIG. 1), the outline of the sensing area 110a is substantially rectangular, and the sensing area 110a has four corners C1, C2, C3, and C4 in a top view direction and four edges E1, E2, E3, and E4. The edge E1 and the edge E3 are opposite to each other, and the edge E2 and the edge E4 are opposite to each other. The edge E2 connects the edge E1 and the edge E3, and the edge E4 connects the edge E1 and the edge E3. The corner C1 is formed by the intersection of the edge E1 and the edge E2, the corner C2 is formed by the intersection of the edge E2 and the edge E3, the corner C3 is formed by the intersection of the edge E3 and the edge E4, and the corner C4 is formed by the intersection of the edge E1 and the edge E4. The corner C1 and the corner C3 are opposite to each other, and the corner C2 and the corner C4 are opposite to each other. In addition, in the embodiment, the edge E1, the edge E2, the edge E3, and the edge E4 have a length L1, a length L2, a length L3, and a length L4, respectively. The length L1, the length L2, the length L3, and the length L4 are, for example, 5000 microns (μm), but not limited thereto.

The normal pixels 120 are disposed in the sensing area 110a and configured to sense light signals. The normal pixel 120 at least includes a transistor (not shown) and a photosensitive element (not shown). In the embodiment, the photosensitive element may be, for example, an optoelectronic semiconductor (such as a photodiode), and is configured to detect the number of photons of incident light and generate electrical signals, but is not limited thereto. Since the transistor in the normal pixel 120 may be electrically connected to the photosensitive element, the electrical signal of the photosensitive element may be sent out through the transistor, so that the X-ray sensing module 100 may receive the electrical signal from the transistor and present the image sensed by the normal pixel 120. In the embodiment, the photosensitive element may be, for example, a stacked structure composed of a P-type semiconductor, an intrinsic semiconductor, and an N-type semiconductor, but is not limited thereto.

The dark pixels 130 and 130a may be regarded as pixels where the X-ray sensing module 100 cannot receive electrical signals, and may be regarded as dark spots where images cannot be presented. In the embodiment, the dark pixel 130 and the dark pixel 130a may be respectively disposed at different positions in the sensing area 110a. For example, the dark pixel 130 may be adjacent to the corner C1, and the dark pixel 130a may be adjacent to the corner C3. The dark pixel 130 may be adjacent to the edge E1 and/or the edge E4, and the dark pixel 130 does not touch the edge E1 and/or the edge E4. The dark pixel 130a may be adjacent to the edge E2 and/or the edge E3, and the dark pixel 130a does not touch the edge E2 and/or the edge E3. The dark pixel 130 and the dark pixel 130a may be located substantially on the line connecting the corner C2 and the corner C4 (that is, a diagonal line of the sensing area 110a), but not limited thereto. In some embodiments, the dark pixel 130 and the dark pixel 130a are disposed adjacent to the corner C2 and the corner C4, respectively, and away from the middle of the sensing area 110a, but not limited thereto. It should be noted that the middle of the sensing area 110a may be a radius of 1 cm to 5 cm at the point where two diagonal lines of the sensing area 110a intersect, but is not limited thereto. For example, the middle of the sensing area 110a may be a range covered by a circle whose center is the intersection point of two diagonal lines of the sensing area 110a and whose radius is 1 cm to 5 cm.

In addition, in the embodiment, a distance D1 exists between the dark pixel 130 and the edge E1 of the sensing area 110a, a distance D2 exists between the dark pixel 130 and the edge E4 of the sensing area 110a, a distance D3 exists between the dark pixel 130a and the edge E2 of the sensing area 110a, a distance D4 exists between the dark pixel 130a and the edge E3 of the sensing area 110a, and the distance D1 is, for example, ¼ to ⅟350 of the length L1 of the edge E1 (i.e., ⅟350×L1≤D1≤¼×L1), for example: ⅟10, ⅟20, ⅟50, ⅟100, ⅟150, or ⅟200, but not limited thereto. The distance D2 is, for example, ¼ to ⅟350 of the length L4 of the edge E4 (i.e., ⅟350×L4≤D2≤¼×L4), for example: ⅟10, ⅟20, ⅟50, ⅟100, ⅟150, or ⅟200, but not limited thereto. The distance D3 is, for example, ¼ to ⅟₃₅₀ of the length L2 of the edge E2 (i.e., ⅟₃₅₀×L2≤D3≤¼×L2), for example: ⅟₁₀, ⅟₂₀, ⅟₅₀, ⅟₁₀₀, ⅟₁₅₀, or ⅟₂₀₀, but not limited thereto. The distance D4 is, for example, ¼ to ⅟₃₅₀ of the length L3 of the edge E3 (i.e., ⅟₃₅₀×L3≤D4≤¼×L3), for example: ⅟₁₀, ⅟₂₀, ⅟₅₀, ⅟₁₀₀, ⅟₁₅₀, or ⅟₂₀₀, but not limited thereto. The distance D1 is, for example, the minimum distance measured between the dark pixel 130 and the edge E1, the distance D2 is, for example, the minimum distance measured between the dark pixel 130 and the edge E4, the distance D3 is, for example, the minimum distance measured between the dark pixel 130a and the edge E2, and the distance D4 is, for example, the minimum distance measured between the dark pixel 130a and the edge E3. In some embodiments, when the distance (D1, D2, D3, or D4)≤⅟₃₅₀×length (L1, L2, L3, or L4), the dark pixel is too close to the edge of the sensing area 110a to be easily distinguished. In some embodiments, when the distance (D1, D2, D3, or D4)>¼×length (L1, L2, L3, or L4), the dark pixel is too close to the middle of the sensing area 110a, which may cause the risk of an image being misjudged.

Please refer to FIG. 2A. In the schematic cross-sectional view of the dark pixels 130 and 130a in the embodiment, the X-ray sensing module 100 further includes a metal layer 140, a bias signal line 150, an insulating layer 160, an insulating layer 162, an insulating layer 164, an insulating layer 166, a scan line SL, and a data line DL. The dark pixels 130 and 130a include transistors 132 and photosensitive elements 134.

Specifically, the transistor 132 is disposed on the substrate 110. The transistor 132 includes a gate GE, a part of a gate insulating layer GI, a source SD1, and a semiconductor SE, and the transistor 132 does not include a drain, but not limited thereto. The gate GE is disposed on the substrate 110. Taking a bottom-gate type transistor as an example, the gate insulating layer GI is disposed on the gate GE to cover the gate GE and the substrate 110. The semiconductor SE is disposed on the gate insulating layer GI and is disposed corresponding to the gate GE. The source SD1 is disposed on the gate insulating layer GI, and the source SD1 may be electrically connected to the semiconductor SE. In the embodiment, the material of the semiconductor SE may include amorphous silicon, low temperature poly-silicon (LTPS), metal oxide semiconductor (such as indium gallium zinc oxide (IGZO)), other suitable materials or a combination thereof, but not limited thereto. In some embodiments, the structure of the transistor 132 may also be a top-gate type transistor, a double-gate type transistor or other suitable transistors.

The scan line SL and the data line DL are respectively disposed on the substrate 110. The scan line SL is electrically connected to the gate GE of the transistor 132, and the data line DL is electrically connected to the source SD1 of the transistor 132, as shown in the circuit diagram of FIG. 2B. In the embodiment, the normal pixel 120 and the dark pixels 130 and 130a may be defined by the area between two adjacent scan lines SL and two adjacent data lines DL, and the two adjacent scan lines SL may respectively intersect the two adjacent data lines DL.

The insulating layer 160 is disposed on the gate insulating layer GI and disposed between the metal layer 140 and the substrate 110. The insulating layer 160 may cover the source SD1 and the semiconductor SE. In the embodiment, the insulating layer 160 may be a single-layer or multi-layer structure, and may include an organic material (such as polymethyl methacrylate), an inorganic material (such as silicon nitride or silicon oxide or silicon oxynitride) or a combination structure thereof, but not limited thereto.

The metal layer 140 is disposed on the insulating layer 160 and disposed between the photosensitive element 134 and the transistor 132, so that the insulating layer 160 is located between the metal layer 140 and the transistor 132. In the embodiment, since the transistors 132 in the dark pixels 130 and 130a do not include drains (that is, the drain in the transistor 132 is removed), the metal layer 140 in the dark pixels 130 and 130a is in an open circuit state with the transistors 132 (as shown in the circuit diagram of FIG. 2B), and the metal layer 140 is electrically insulated from the transistors 132. The material of the metal layer 140 may include a transparent conductive material or a non-transparent conductive material, such as indium gallium zinc oxide (IGZO), indium-tin oxide (ITO), indium-zinc-oxide (IZO), indium oxide, zinc oxide, tin oxide, metal materials (such as aluminum, molybdenum, copper, titanium, silver, etc.), other suitable materials or a combination thereof, but not limited thereto.

The photosensitive element 134 is disposed on the metal layer 140, and the photosensitive element 134 may be electrically connected to the metal layer 140. The photosensitive element 134 may include a photodiode, a phototransistor, a metal-semiconductor-metal photodetector (MSM photodetector), or any suitable photosensitive element, but is not limited thereto. In the embodiment, the photosensitive element 134 may be an optoelectronic semiconductor and is configured to detect the number of photons of incident light and generate electrical signals. However, since the transistors 132 in the dark pixels 130 and 130a do not include drains and the metal layer 140 may be electrically insulated from the transistors 132, the photosensitive element 134 may also be electrically insulated from the transistor 132, thereby making the electrical signal of the photosensitive element 134 unable to be received by the X-ray sensing module 100, and making the dark pixels 130 and 130a able to be regarded as dark spots and unable to present images.

The insulating layer 162 is disposed on the photosensitive element 134 to cover the metal layer 140 and the insulating layer 160. The insulating layer 162 may have an opening 1621 to expose a part of the photosensitive element 134. The insulating layer 164 is disposed on the insulating layer 162 to cover the insulating layer 162. The insulating layer 164 may have an opening 1641 to connect to the opening 1621 and expose a part of the photosensitive element 134. In the embodiment, the insulating layer 162 and the insulating layer 164 may be a single-layer or multi-layer structure, and the materials of the insulating layer 162 and the insulating layer 164 may be the same as the materials included in the aforementioned insulating layer 160, so the descriptions are not repeated here.

The bias signal line 150 is disposed on the photosensitive element 134 and the insulating layer 164, so that the photosensitive element 134 is disposed between the metal layer 140 and the bias signal line 150. The bias signal line 150 may further be disposed in the opening 1641 of the insulating layer 164 and the opening 1621 of the insulating layer 162, so that the bias signal line 150 may be electrically connected to the photosensitive element 134.

The insulating layer 166 is disposed on the bias signal line 150 to cover the insulating layer 164.

Based on the above, in the X-ray sensing module 100 of the embodiment, the method of disconnection (such as removing the drain of the transistor 132, but not limited thereto) is used to make the at least two pixels at different positions in the sensing area 110a able to be changed into the dark pixels 130 and 130a, so that the X-ray sensing module 100 may use the positions of the at least two dark pixels 130 and 130*a* as the positioning points of each image when taking continuous images to improve the accuracy or precision of positioning. In this way, the positions of the at least two dark pixels 130 and 130*a* of each image may be used to overlap multiple images, so that the accuracy or precision of the overlapped images may be improved.

Figure 4A:
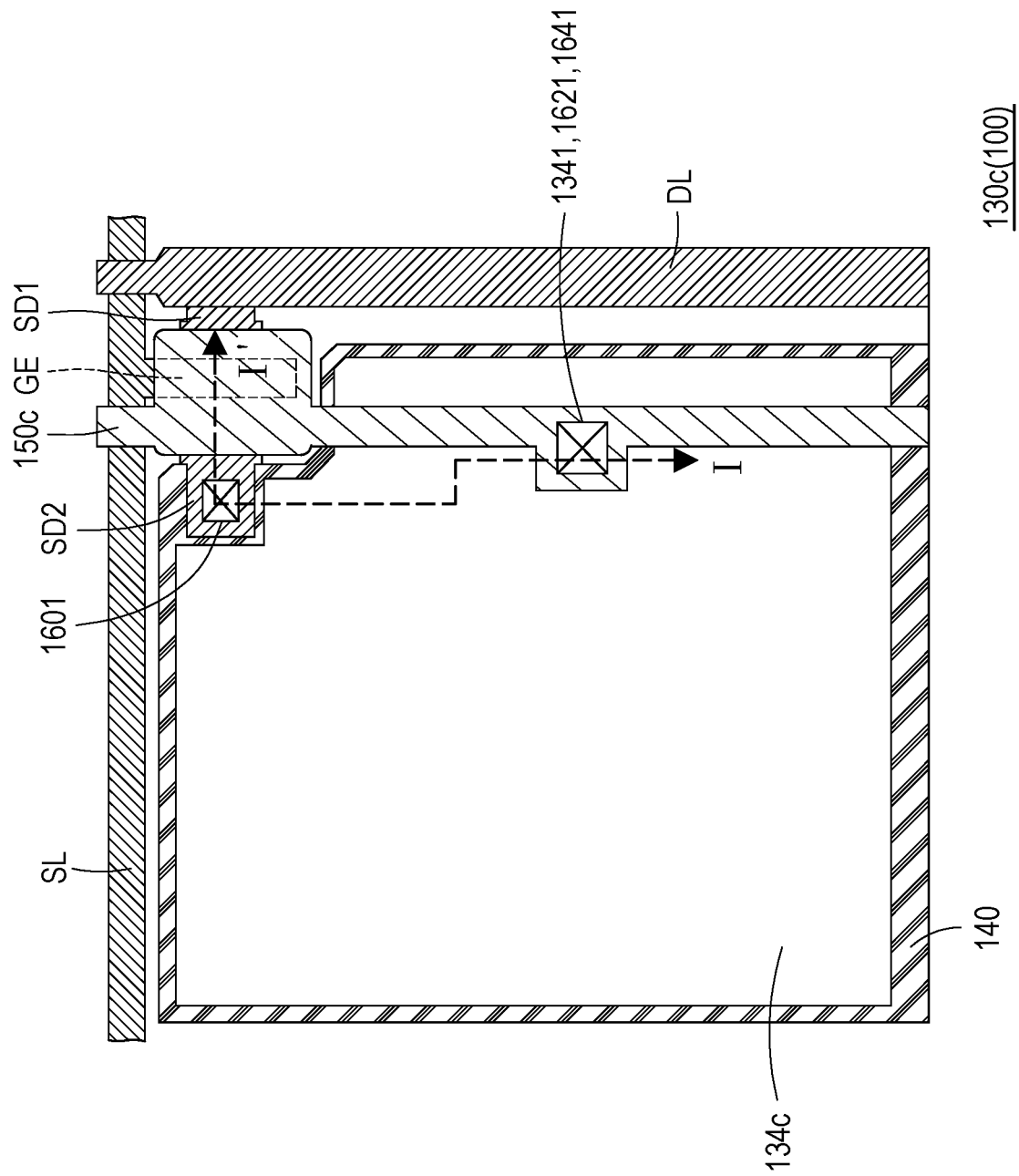
FIG. 4A is a schematic top view of a dark pixel of an X-ray sensing module according to a third embodiment of the disclosure.
Figure 4B:
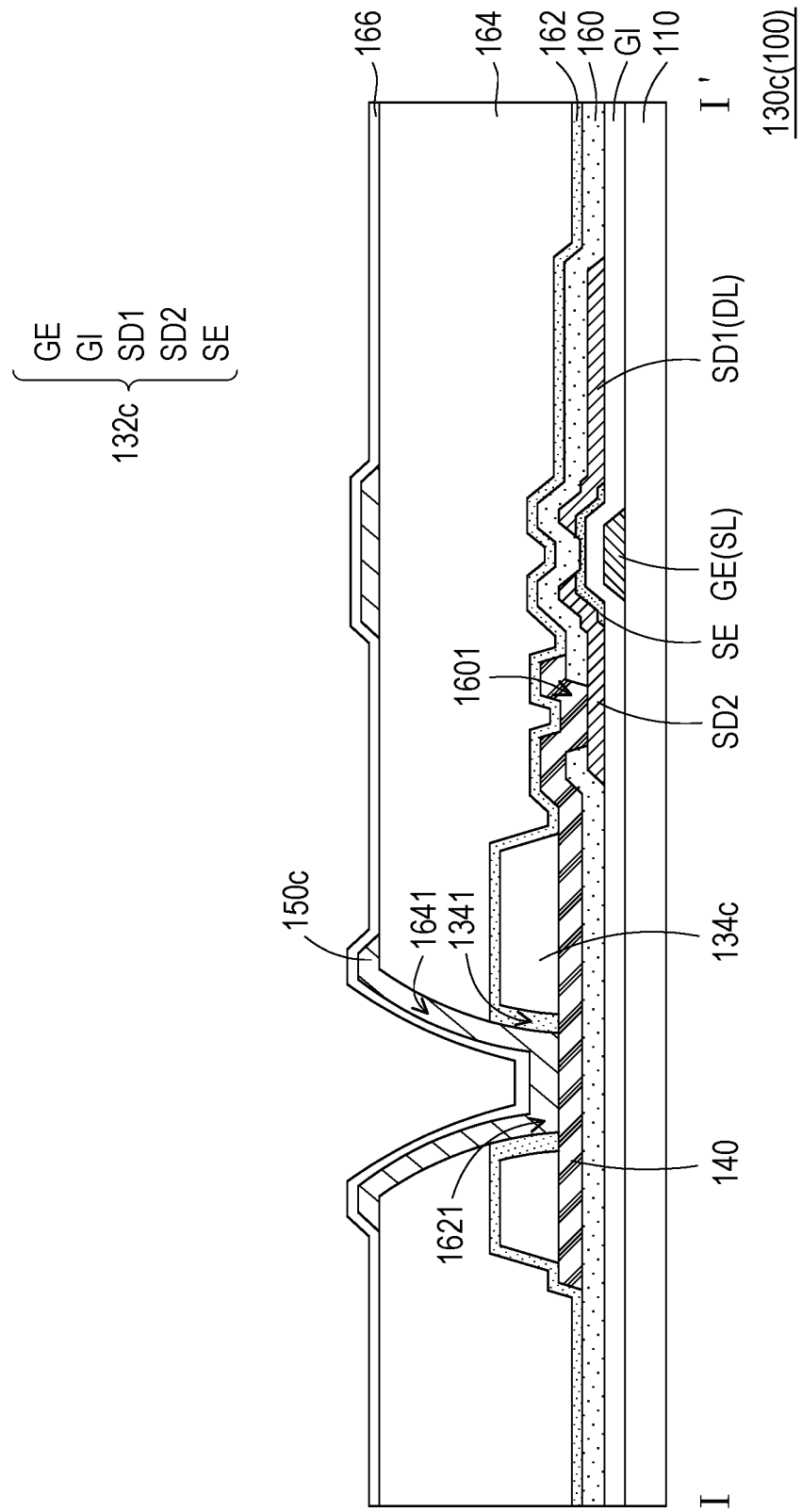
FIG. 4B is a schematic cross-sectional view of the dark pixel in FIG. 4A along a section line I-I'.
Figure 4C:
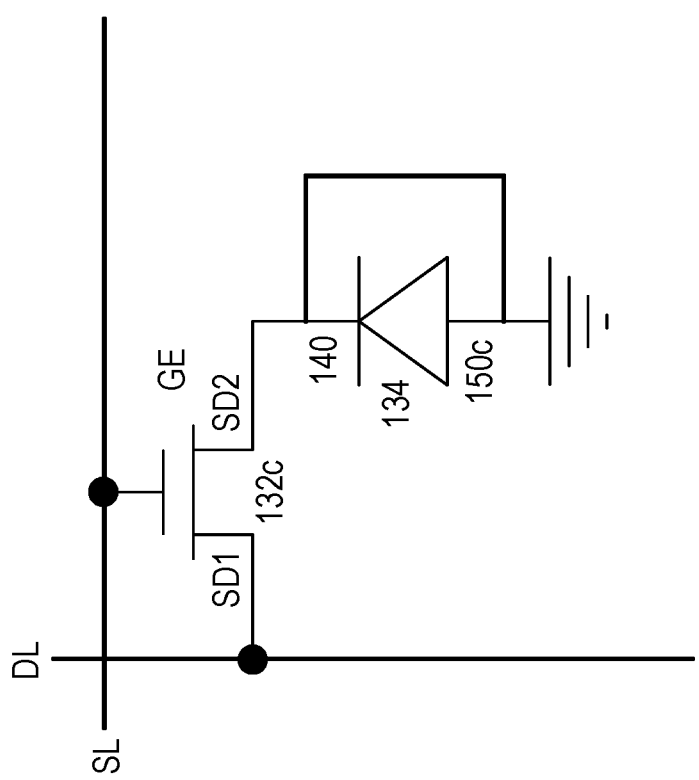
FIG. 4C is a schematic circuit diagram of the dark pixel of the X-ray sensing module shown in FIG. 4B.

In the embodiment, although some pixels in the sensing area 110*a* in the X-ray sensing module 100 may be changed into dark pixels by means of an open circuit, so that the dark pixels may be configured for positioning purposes, but the disclosure does not limit the manner in which dark pixels are formed. In some embodiments, a short circuit may also be used to form dark pixels, as shown in FIGS. 4A to 4C.

In the embodiment, although the outline of the sensing area 110*a* is substantially rectangular, the disclosure does not limit the outline shape of the sensing area, as long as the sensing area may be configured to sense light signals.

In the embodiment, although the two dark pixels 130 and 130*a* are schematically taken as an example in the sensing area 110*a*, the disclosure does not limit the number of dark pixels in the sensing area, as long as the dark pixels are respectively disposed at different positions in the sensing area, and the distance between the dark pixel and the edge of the sensing area is ¼ to ⅟₃₅₀ of the length of the edge. In some embodiments, there may be three or more dark pixels in the sensing area. For example, the sensing area may, for example, have four dark pixels, and the four dark pixels may, for example, be disposed adjacent to four corners, respectively, but not limited thereto.

Other embodiments are described below for illustrative purposes. It must be noted here that the following embodiments use the element numerals and part of the contents of the foregoing embodiments, the same numerals are used to denote the same or similar elements, and the description of the same technical content is omitted. For the description of the omitted parts, reference may be made to the foregoing embodiments, and thus the description is not repeated in the following embodiments.

Figure 3A:
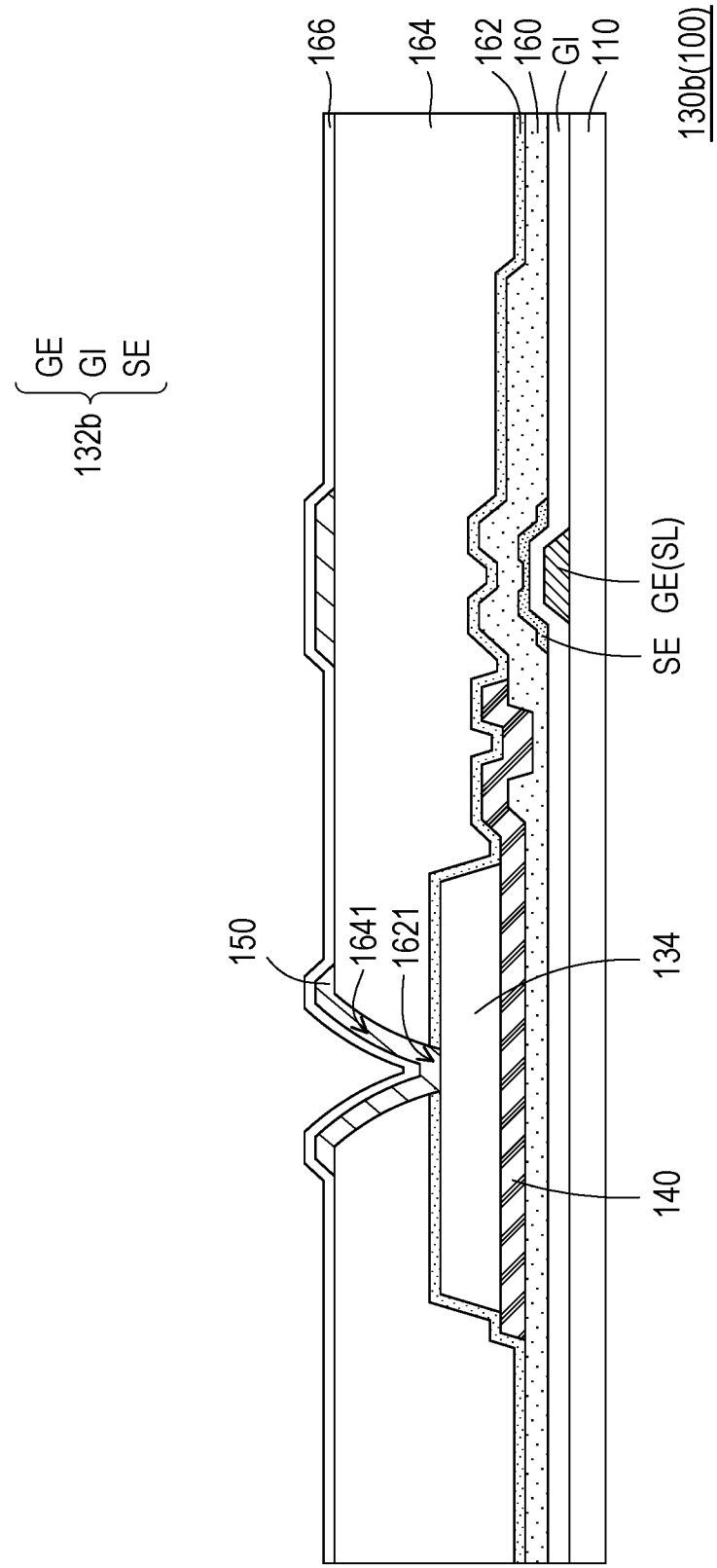
FIG. 3A is a schematic cross-sectional view of a dark pixel of an X-ray sensing module according to a second embodiment of the disclosure.
Figure 3B:
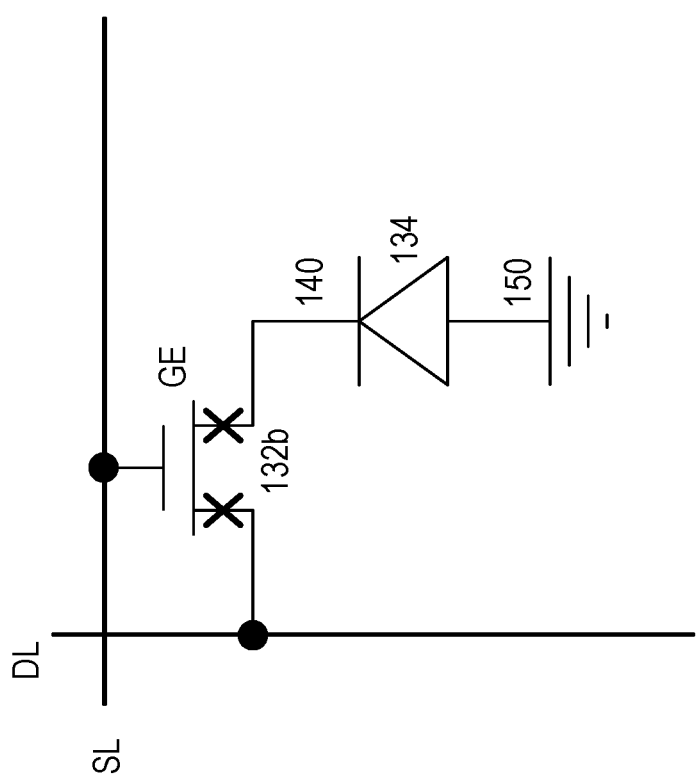
FIG. 3B is a schematic circuit diagram of the dark pixel in FIG. 3A.

FIG. 3A is a schematic cross-sectional view of a dark pixel of an X-ray sensing module according to a second embodiment of the disclosure. FIG. 3B is a schematic circuit diagram of the dark pixel in FIG. 3A. Please refer to FIGS. 2A to 2B and FIGS. 3A to 3B at the same time. A dark pixel 130*b* in the embodiment is similar to the dark pixels 130 and 130*a* in FIG. 2A, but the main difference between the two is: in the dark pixel 130*b* of the X-ray sensing module 100 in the embodiment, a transistor 132*b* does not include a source (that is, both the source and the drain of the transistor 132*b* are removed).

Specifically, please refer to FIGS. 3A and 3B at the same time. In the embodiment, since the transistor 132*b* in the dark pixel 130*b* does not include a source and a drain, the metal layer 140 in the dark pixel 130*b* is in an open circuit state with the transistor 132*b*, so that the photosensitive element 134 is electrically insulated from the transistor 132*b*, and the dark pixel 130*b* may be regarded as a dark spot.

FIG. 4A is a schematic top view of a dark pixel of an X-ray sensing module according to a third embodiment of the disclosure. FIG. 4B is a schematic cross-sectional view of the dark pixel in FIG. 4A along a section line I-I'. FIG. 4C is a schematic circuit diagram of the dark pixel of the X-ray sensing module shown in FIG. 4B. Please refer to FIGS. 2A to 2B and FIGS. 4B to 4C at the same time. A dark pixel 130*c* in the embodiment is similar to the dark pixels 130 and 130*a* in FIG. 2A, but the main difference between the two is: in the dark pixel 130*c* of the X-ray sensing module 100 in the embodiment, the metal layer 140 may be electrically connected to a transistor 132*c* and a bias signal line 150*c*.

Specifically, please refer to FIGS. 4A and 4B at the same time. In the embodiment, in the X-ray sensing module 100, the transistor 132 may further include a conductive element SD2. That is to say, the conductive element SD2 may be the drain of the transistor 132*c*. In addition, the conductive element SD2 may be disposed between the gate insulating layer GI and the insulating layer 160 and electrically connected to the semiconductor SE.

The insulating layer 160 is disposed between the metal layer 140 and the substrate 110, and the insulating layer 160 may have an opening 1601 to expose a part of the conductive element SD2. The metal layer 140 may further be disposed in the opening 1601 of the insulating layer 160, so that the metal layer 140 may be electrically connected to the conductive element SD2, and the metal layer 140 may be electrically connected to the transistor 132*c* through the conductive element SD2.

In addition, in the embodiment, a part of a photosensitive element 134*c* is removed to form an opening 1341, and the opening 1341 may expose a part of the metal layer 140. The insulating layer 162 may further be disposed on the opening 1341 of the photosensitive element 134*c*. The insulating layer 162 may have an opening 1621 to expose a part of the metal layer 140. The opening 1641 of the insulating layer 164 may be connected to the opening 1621 of the insulating layer 162, and the bias signal line 150 may further be disposed in the opening 1641 of the insulating layer 164 and the opening 1621 of the insulating layer 162, so that the bias signal line 150 may be in contact with and electrically connected to the metal layer 140. The bias signal line 150*c* may be disposed in the opening 1341 of the photosensitive element 134*c*, so that the bias signal line 150*c* may pass through the photosensitive element 134*c*.

In the embodiment, since the bias signal line 150*c* may pass through the photosensitive element 134*c* and be electrically connected to the metal layer 140, the bias signal line 150*c* is in a short circuit state with the metal layer 140 (as shown in FIG. 4C), so that the photosensitive element 134*c* cannot convert a light signal into an electrical signal, and the dark pixel 130*c* may be regarded as a dark spot and cannot present an image.

In the embodiment, although the bias signal line 150*c* is electrically connected to the metal layer 140 by removing a part of the photosensitive element 134*c* to form the opening 1341, the disclosure does not limit the method by which the bias signal line 150*c* may be electrically connected to the metal layer 140. In some embodiments, a method of not providing a photosensitive element may also be used to make the bias signal line able to be electrically connected to the metal layer.

To sum up, in the X-ray sensing module of an embodiment of the disclosure, at least two pixels at different positions in the sensing area may be changed into dark pixels by means of an open circuit or a short circuit, so that when the X-ray sensing module takes continuous images, the positions of at least two dark pixels may be used as the positioning points of each image, so as to improve the accuracy or precision of positioning. In addition, in the embodiment, by making the distance between the at least two dark pixels and the edge of the sensing area be ¼ to ⅟₃₅₀ of the length of the edge, the dark pixels are not too close to the edge of the sensing area and are not easy to be distinguished, and the dark pixels are not too close to the middle of the sensing area, which may cause the risk of images being misjudged.

Although the disclosure has been described with reference to the above embodiments, the described embodiments are not intended to limit the disclosure. People of ordinary skill in the art may make some changes and modifications without departing from the spirit and the scope of the disclosure. Thus, the scope of the disclosure shall be subject to those defined by the attached claims.

What is claimed is:

1. An X-ray sensing module, comprising:
   a substrate, comprising a sensing area, wherein the sensing area has four corners in a top view direction;
   a plurality of normal pixels, disposed in the sensing area and configured to sense light signals; and
   at least two dark pixels, respectively disposed at different positions in the sensing area,
   wherein a distance between the at least two dark pixels and an edge of the sensing area is 1/4 to 1/350 of a length of the edge.

2. The X-ray sensing module according to claim 1, wherein the at least two dark pixels are four dark pixels, and the four dark pixels are adjacently disposed at the four corners.

3. The X-ray sensing module according to claim 1, wherein the X-ray sensing module further comprises a metal layer, and one of the at least two dark pixels comprises:
   a transistor, disposed on the substrate; and
   a photosensitive element, disposed on the metal layer,
   wherein the metal layer is electrically connected to the photosensitive element, and the metal layer is electrically insulated from the transistor.

4. The X-ray sensing module according to claim 3, further comprising:
   a bias signal line, disposed on the photosensitive element, wherein the photosensitive element is disposed between the metal layer and the bias signal line.

5. The X-ray sensing module according to claim 3, wherein the photosensitive element is electrically insulated from the transistor.

6. The X-ray sensing module according to claim 3, wherein the transistor does not comprise a drain.

7. The X-ray sensing module according to claim 3, wherein the transistor does not comprise a drain and a source.

8. The X-ray sensing module according to claim 1, wherein the X-ray sensing module further comprises a metal layer, and one of the at least two dark pixels comprises:
   a transistor, disposed on the substrate; and
   a photosensitive element, disposed on the metal layer,
   wherein the metal layer is electrically connected to the photosensitive element and the transistor.

9. The X-ray sensing module according to claim 8, further comprising:
   a bias signal line, passing through the photosensitive element and electrically connected to the metal layer.

10. The X-ray sensing module according to claim 8, wherein the bias signal line is in contact with the metal layer.

11. The X-ray sensing module according to claim 8, further comprising:
    an insulating layer, disposed between the metal layer and the substrate.

12. The X-ray sensing module according to claim 11, wherein the transistor further comprises a conductive element, and the conductive element is electrically connected to the metal layer.

13. The X-ray sensing module according to claim 1, wherein the at least two dark pixels are respectively adjacent to two of the four corners and away from a middle of the sensing area.

14. The X-ray sensing module according to claim 13, wherein the two of the four corners are opposite to each other.

15. The X-ray sensing module according to claim 14, wherein the at least two dark pixels are disposed on a connecting line between the two corners.

16. The X-ray sensing module according to claim 13, wherein the middle is a range covered by a circle whose center is an intersection point of two diagonal lines of the sensing area and whose radius is 1 cm to 5 cm.

17. The X-ray sensing module according to claim 1, wherein the at least two dark pixels are dark spots.

18. The X-ray sensing module according to claim 1, wherein the at least two dark pixels cannot present images.

19. The X-ray sensing module according to claim 1, wherein the distance between the at least two dark pixels and the edge of the sensing area is 1/10 to 1/200 of the length of the edge.

20. The X-ray sensing module according to claim 1, wherein the at least two dark pixels do not touch the edge.

* * * * *